(12) United States Patent
Schneider et al.

(10) Patent No.: US 9,394,558 B2
(45) Date of Patent: Jul. 19, 2016

(54) METHODS FOR EXTRACTION AND PURIFICATION OF GANGLIOSIDES

(75) Inventors: Jay S. Schneider, Cherry Hill, NJ (US); Gerri Henwood, Malvern, PA (US); Robert Florentine, Naples, FL (US); Christopher Barber, Audobon, PA (US)

(73) Assignee: LZ Therapeutics, Inc., Malvern, PA (US)

(*) Notice: Subject to any disclaimer, the term of this patent is extended or adjusted under 35 U.S.C. 154(b) by 556 days.

(21) Appl. No.: 13/407,067

(22) Filed: Feb. 28, 2012

(65) Prior Publication Data
US 2012/0220763 A1 Aug. 30, 2012

Related U.S. Application Data

(63) Continuation of application No. PCT/US2010/047522, filed on Sep. 1, 2010.

(60) Provisional application No. 61/238,775, filed on Sep. 1, 2009.

(51) Int. Cl.
| | |
|---|---|
| C12N 5/07 | (2010.01) |
| C12N 5/079 | (2010.01) |
| C12P 1/00 | (2006.01) |
| C12P 19/44 | (2006.01) |
| A61K 31/7032 | (2006.01) |
| G01N 33/92 | (2006.01) |
| C12P 19/26 | (2006.01) |

(52) U.S. Cl.
CPC ........... *C12P 19/44* (2013.01); *C12P 19/26* (2013.01)

(58) Field of Classification Search
None
See application file for complete search history.

(56) References Cited

U.S. PATENT DOCUMENTS

| | | | |
|---|---|---|---|
| 4,713,374 A | 12/1987 | Della Valle | |
| 5,296,360 A | 3/1994 | Sugimori et al. | |
| 5,532,141 A | 7/1996 | Holler | |
| 5,635,504 A | 6/1997 | Ryono et al. | |
| 5,788,985 A | 8/1998 | Rodriguez et al. | |
| 5,922,773 A | 7/1999 | Lipton et al. | |
| 6,440,703 B1 | 8/2002 | DeFrees | |
| 7,851,451 B2 | 12/2010 | Clandinin | |
| 2002/0068080 A1 | 6/2002 | Lerner | |
| 2003/0087396 A1 | 5/2003 | Saito | |
| 2004/0157926 A1 | 8/2004 | Heresco-Levy et al. | |
| 2005/0221380 A1 | 10/2005 | Muthing et al. | |
| 2006/0142241 A1 | 6/2006 | Yoo | |
| 2007/0117778 A1 | 5/2007 | Ilan | |
| 2007/0224200 A1 | 9/2007 | Elbawab et al. | |
| 2008/0064709 A1 | 3/2008 | Krishnan | |
| 2012/0220543 A1 | 8/2012 | Schneider et al. | |
| 2012/0220544 A1 | 8/2012 | Schneider et al. | |
| 2013/0190257 A1 | 7/2013 | Ragaglia | |
| 2013/0261067 A1 | 10/2013 | Ragaglia et al. | |
| 2015/0025234 A1 | 1/2015 | Ragaglia | |

FOREIGN PATENT DOCUMENTS

| | | |
|---|---|---|
| CN | 135112 | 6/2002 |
| EP | 0713879 | 5/1996 |
| EP | 0661061 A3 | 12/1996 |
| EP | 2011799 A1 | 1/2009 |
| RU | 2483736 | 6/2013 |
| WO | 9803529 A1 | 1/1998 |
| WO | WO 2004/083387 A2 | 9/2004 |
| WO | 2007006157 A1 | 1/2007 |
| WO | 2008034815 A1 | 3/2008 |
| WO | WO 2011/028795 A2 | 3/2011 |

OTHER PUBLICATIONS

Svennerholm, J Neurochem, 10:613-623, 1963.*
Matsuda et al., Glycoconjugate Journal, 14: 729-736, 1997.*
Nilsson et al., Glycoconjugate Journal, 1:43-49, 1984.*
Ahern-Rindell et al., Somatic Cell and Mol Gen., 15(6):525-533, 1989.*
Schengrund and Kovac, Journal of Lipid Res., 40:160-163, 1999.*
Osborne, et al., "Neuroprotection in Relation to Retinal Ischemia and Relevance to Glaucoma," Survey of Opthamology 43(1): pp. S102-S128 (Jun. 1999).
Dreyfus, H., et al., "Gangliosides and Neurotrophic Growth Factors in the Retina," Annals of the New York Academy of Sciences, 845(1): pp. 240-252 (1998).
Norido, F., et al., "Monosialoganglioside (GM1) Treatment of Ouabain-Induced Retinopathy in the Rabbit," Acta Neuropathological, 62(1/2): pp. 46-50 (1983).
Schneider, J.S., "GM1 Ganglioside in the Treatment of Parkinson's Disease," Annuals of the New York Academy of Sciences, 845(1): pp. 363-373 (1998).
Ariga, T., et al., "Role of Ganglioside Metabolism in the Pathogenesis of Alzheimer's Disease—A Review," Journal of Lipid Research, 49(6): pp. 1157-1175 (2008).
Rothblat, et al., The Effects of L-Deprenyl Treatment, Alone and Combined with GM1 Ganglioside, on Striatal Dopamine Content and Substantia Nigra Pars Compacta Neurons, Brain Research 779(1/2): pp. 226-230 (1998).
New, P., "Radiation Injury to the Nervous System," Current Opinion in Neurology 14(6): pp. 725-734 (2001).
Ledeen, R.W., et al., "Gangliosides as Neurotrophic Agents: Studies on the Mechanism of Action," Acta Neurobiol Exp., 50, pp. 439-449 (1990).
Di Gregorio, F., et al., "Efficacy of Ganglioside Treatment in Reducing Functional Alterations Induced by Vincristine in Rabbit Peripheral Nerves," Cancer Chemother Pharmacol 26: pp. 31-36 (1990).

(Continued)

*Primary Examiner* — Daniel E Kolker
*Assistant Examiner* — Stacey N MacFarlane
(74) *Attorney, Agent, or Firm* — Medler Ferro Woodhouse & Mills PLLC

(57) ABSTRACT

Methods for purification and extraction of GM1 ganglioside from cells derived from sheep afflicted with GM1 gangliosidosis or from cells derived from human patients with GM1 gangliosidosis as stable and renewable sources of GM1.

17 Claims, 7 Drawing Sheets

(56) References Cited

OTHER PUBLICATIONS

Pinsky, L., et al., "GM1 Gangliosides in Skin Fibroblast Culture: Enzymatic Differences between Types 1 and 2 and Observations on a Third Variant," Am. J. Hum. Genet., 26, pp. 563-577 (1974).
Vanna Chigorno, et al., "Formation of a Cytosolic Ganglioside-Protein Complex Following Administration of Photoreactive Ganglioside GM1 to Human Fibroblasts in Culture," FEBS. 263(2): pp. 329-331 (1990).
Gu, Y., et al., "Silencing of GM3 Synthase Suppresses Lung Metastasis of Murine Breast Cancer Cells," online at http://breast-cancer-research.com/content/10/1/R1 pp. 1-12 (2008).
Ladisch, S., "Shedding and Immunoregulatory Activity of YAC-1 Lymphoma Cell Gangliosides," Cancer Research 43, pp. 3808-3813 (Aug. 1983).
Kumbale, R., et al., "GM1 Delivery to the CSF Via the Olfactory Pathway," Drug Delivery, 6: pp. 23-30 (1999).
Yuyama, K., et al., "Chloroquine-induced Endocytic Pathway Abnormalities: Cellular Model of GM1 Ganglioside-Induced Ab fibrillogenesis in Alzheimer's Disease," Federation of European Biochemical Societies Letters, 580, pp. 6972-6976 (2006).
Yuyama, K., et al., "Accelerated Release of Exosome-Associated GM1 Ganglioside (GM1) by Endocytic Pathway Abnormality: another putative pathway for GM1-induced amyloid fibral formation," Journal of Neurochemistry 105, pp. 217-224 (2008).
Peng, Y., et al., "Development of a Large Scale Process for the Conversion of Polysialogangliosides to Monosialotetrahexosylganglioside with a Novel Strain of *Brevibacterium casei* Producing Sialidase," Biotechnol Letters 29: pp. 885-889 (2007).
Taketomi, T., et al. "Matrix-assisted Laser Desorption Ionization Time-of-Flight Mass Spectrometric Analysis of Glycosphingolipids Including Gangliosides," Acta Biochimica Polonica 45: pp. 987-999 (1998).
Ackerman et al., "Differential expression of surface monosialoganglioside GM1 in various hemic cell lines of normal human bone marrow. A quantitative immunocytochemical study using the cholera toxin-gold-labeled anti-cholera toxin procedure," J. Histochem. Cytochem. 28:1334-1342 (1980).
Christie, "Ganglioside," The AOCS Lipid Library, last updated Jul. 23, 2012.
Dijkhuis et al., "Gangliosides do not affect ABC transporter function in human neuroblastoma cells," J. Lipid Res. 47:1187-1195 (2006).
Freund et al., "Differential expression of biofunctional GM1 and GM3 gangliosides within the plastic-adherent multipotent mesenchymal stromal cell population," Cytotherapy 12:131-142 (2010).
Hirata et al., "Chloroquine inhibits glutamate-induced death of a neuronal cell line by reducing reactive oxygen species through sigma-1 receptor," J. Neurochem, 119:839-847 (2011).
Ikeda et al., "Targeted analysis of ganglioside and sulfatide molecular species by LC/ESI-MS/MS with theoretically expanded multiple reaction monitoring," J. Lipid Res. 49:2678-2689 (2008).
Kolter et al., "Combinatorial Ganglioside Biosynthesis," Journal of Biological Chemistry 277(29):25859-25862 (2002).
Kwak, et al., "Dynamic changes of gangliosides expression during the differentiation of embryonic and mesenchymal stem cells into neural cells," Exp. Mol. Med. 38(6):668-676 (2006).
Lauer et al., "Analysis of cholera toxin-ganglioside interactions by flow cytometry,," Biochemistry 41:1742-1751 (2002).

Maccioni et al., "The biosynthesis of gangliosides. Labeling of rat brain gangliosides in vivo," Biochem J. 125:1131-1137 (1971).
Masserini and Freire, "Thermotropic Characterization of Phosphatidylcholine Vesicles Containing Ganglioside GM1 with Homogeneous Ceramide Chain Length," Biochem. 25:1043-1049 (1986).
Masson et al., "Glucosamine induces cell-cycle arrest and hypertrophy of messangial cells: implication of gangliosides" Biochem. J, 388:537-544 (2005).
Miller-Podraza et al., "Biosynthesis and localization of gangliosides in cultured cells," Biochem. 21:3260-3265 (1982).
Nishio et al., "Overexpressed GM1 Suppresses Nerve Growth Factor (NGF) Signals by Modulating the Intracellular Localization and NGF Receptors and Membrane Fluidity in PC12 Cells," J. Biol. Chem. 279:33368-33378 (2004).
Parton, R.G., "Ultrastructural Localization of Gangliosides; GM1 is Concentrated in Caveolae," J. Histochem. Cytochem. 42(2):155-166 (1994).
Schneider et al., "Parkinson's disease improved function with GM1 ganglioside treatment in a randomized placebo-controlled study," Neurology 50(6):1630-1636 (1998).
Schneider et al., "GM1 ganglioside in Parkinson's disease: results of a five year open study," J. Neurol. Sci. 292:45-51 (2010).
Sonnino and Chigorno, "Ganglioside molecular species containing C18- and C20-sphingosine in mammalian nervous tissues and neuronal cell cultures," Biochem. Biophys. Acta. 1469:63-77 (2000).
Tio et al., "Roles of db-cAMP, IBMX and RA in Aspects of Neural Differentiation of Cord Blood Derived Mesenchymal-Like Stem Cells," PLoS ONE 5(2):1-11 (2010).
Xu et al., "Multi-system disorders of glycosphingolipid and ganglioside metabolism," J. Lipid Res. 51:1643-1675 (2010).
Parrinello et al, "Oxygen Sensitivity Severely Limits the Replicative Lifespan of Murine Fibroblasts," Nature Cell Biology 5(8):741-747 (2003).
Pullarkat et al., "Ganglioside accumulation in cultured skin fibroblasts from gangliosidosis patients," Biochemical and Biophysical Research Communications, 92(1):149-154 (1980).
Asou et al., "Ganglioside Composition of Growth Cone-Deficient Nerve Cell Cultures," Cell Structure and Functions, 12:165-171 (1987).
Asou et al., "Growth Cones in Developing Cultured Cortical Neurons," Cell Structure and Functions, 12:73-81 (1987).
Friedenstein, A.J., "Stromal Mechanisms of Bone Marrow: Cloning in Vitro and Retransplantation in Vivo," Immunobiology of Bone Marrow Transplantation, 25:19-29 (1980).
Schwarzmann et al., "In Vitro Corporation and Metabolism of Gangliosides," Gangliosides and Modulation of Neuronal Functions, NATO ASI Series, H7:219-229 (1987).
Machine Translation of RU2483736 (2013) from WIPO.
Machine Translation of CN1353112 (2002) from WIPO.
Dawson, "Regulation of glycosphingolipid metabolism in mouse neuroblastoma and glioma cell lines. Comparison of glioma (oligodendroglioma-like) with neuroblastoma cell lines." *J. Biol. Chem.* 254:155-162 (1979).
Deng et al., "In Vitro Differentiation on Human Marrow Stromal Cells into Early Progenitors of Neural Cells by Conditions That Increase Intracellular Cyclic AMP" *Biochem Biophy Res Comm* 282:148-152, 2001.
Yamamoto et al., "GM1-ganglioside-induced Aβ assembly on synaptic membranes of cultured neurons," *Biochimica et Biophysica Acta 1768*: 1128-1137 (2007).

* cited by examiner

Sheep hippocampal Neural Progenitors Culture Expanded in low O2, low density, Media Type #1

| Tube # | O₂ Level | Growth Medium | Seeding Density | Passage | # of Flasks | Seed Date | Seed Cell # | Cell Count (Harvest) | Viability (%) | TVC | Mean Dbl | Total Dbl | Passage Time (Hr) | Dbl Time ($T_D$) | Harvest Date |
|---|---|---|---|---|---|---|---|---|---|---|---|---|---|---|---|
| 3 | Low | Media Type #1 | 100,000/cm² | 0 | 1 (T80) | 29-Sep-09 | 8.000E+06 | 2.75E+06 | | | | | | | 9-Oct-09 |
| | | | 100/cm² | 1 | 2 (T225) | 9-Oct-09 | 4.500E+04 | 8.58E+05 | 97.5% | 8.37E+05 | -1.54 | -1.54 | 257 | -166.8 | 15-Oct-09 |
| | | | | 2 | 3 (T225) | 15-Oct-09 | 6.750E+04 | 2.99E+07 | 97.7% | 2.92E+07 | 4.22 | 4.22 | 144.5 | 34.3 | 21-Oct-09 |
| | | | | 3 | 3 (T225) | 21-Oct-09 | 6.750E+04 | 2.07E+07 | 94.5% | 1.95E+07 | 8.76 | 12.97 | 144 | 16.4 | 27-Oct-09 |
| | | | | 4 | 3 (T225) | 27-Oct-09 | 3.66E+06 | | 94.5% | 3.46E+06 | 8.18 | 21.15 | 144 | 17.6 | 2-Nov-09 |
| | | | | 5 | 3 (T225) | 2-Nov-09 | 6.750E+04 | 1.05E+06 | 92.9% | 9.74E+05 | 5.68 | 26.83 | 143 | 25.2 | 9-Nov-09 |
| | | | | 6 | 3 (T225) | 9-Nov-09 | 6.750E+04 | 2.50E+05 | 90.2% | 2.26E+05 | 3.85 | 30.68 | 167 | 43.4 | 17-Nov-09 |
| | | | | | | | | | | | 1.74 | 32.42 | 188 | 108.0 | |

FIG. 1

Hippocampal Neural Progenitors Culture Expanded in Low O2, Low Seeding Density, and Media Type #1

Total Doublings

| Passage | Hippocampal Neural Progenitors |
|---|---|
| Passage 0 | -1.54 |
| Passage 1 | 4.22 |
| Passage 2 | 12.97 |
| Passage 3 | 21.15 |
| Passage 4 | 26.83 |
| Passage 5 | 30.68 |
| Passage 6 | 32.42 |

Yields

| Passage | Hippocampal Neural Progenitors |
|---|---|
| Passage 0 | 2.75E+06 |
| Passage 1 | 8.37E+05 |
| Passage 2 | 2.92E+07 |
| Passage 3 | 1.95E+07 |
| Passage 4 | 3.46E+06 |
| Passage 5 | 9.74E+05 |
| Passage 6 | 2.26E+05 |

FIG. 3

Sheep Fibroblast Expansion Summary

| Tissue | O₂ Level | Growth Medium | Seeding Density | Passage | # of Flasks | Seed Date | Seed Cell # | Cell Count (Harvest) | Viability (%) | TVC | Mean Dbl | Total Dbl | Passage Time (Hr) | Dbl Time ($T_D$) | Harvest Date | Frozen |
|---|---|---|---|---|---|---|---|---|---|---|---|---|---|---|---|---|
| Lung | Low | FGM-2 | 100,000/cm² | 0 | 3 (T80) | 29-Sep-09 | 1.250E+07 | 7.26E+06 | | | -0.78 | -0.78 | 161 | -205.4 | 5-Oct-09 | 2x 3.6e6 |
| | | | 100/cm² | 1 | 3 (T225) | 5-Oct-09 | 6.750E+04 | 1.07E+07 | 90.7% | 9.67E+06 | 7.30 | 7.30 | 167.5 | 22.9 | 12-Oct-09 | 8 x 1.2e6 |
| | | | | 2 | 3 (T225) | 12-Oct-09 | 6.750E+04 | 5.82E+06 | 93.2% | 5.43E+06 | 6.43 | 13.73 | 120 | 18.7 | 17-Oct-09 | 4 x 1.3e6 |
| | | | | 3 | 3 (T225) | 17-Oct-09 | 6.750E+04 | 5.27E+06 | 94.6% | 4.99E+06 | 6.29 | 20.02 | 146 | 23.2 | 23-Oct-09 | 4 x 1.2e6 |
| | | | | 4 | 3 (T225) | 23-Oct-09 | 6.750E+04 | 8.50E+06 | 93.8% | 7.97E+06 | 6.98 | 27.00 | 142.5 | 20.4 | 29-Oct-09 | 7 x 1.1e5 |
| | | | | 5 | 3 (T225) | 29-Oct-09 | 6.750E+04 | 6.30E+06 | 95.4% | 6.01E+06 | 6.55 | 33.54 | 144 | 22.0 | 4-Nov-09 | 5 x 1.1e6 |
| | | | | 6 | 3 (T225) | 4-Nov-09 | 6.750E+04 | 6.60E+06 | 97.4% | 6.43E+06 | 6.61 | 40.15 | 168 | 25.4 | 11-Nov-09 | 5 x 1.1e6 |
| | | | | 7 | 3 (T225) | 11-Nov-09 | 6.750E+04 | 5.33E+06 | 94.2% | 5.02E+06 | 6.30 | 46.46 | 165 | 26.2 | 18-Nov-09 | 5 x 1.1e6 |
| | | | | 8 | 3 (T225) | 18-Nov-09 | 6.750E+04 | 3.60E+06 | 93.0% | 3.35E+06 | 5.74 | 52.19 | 142 | 24.8 | 24-Nov-09 | 3 x 1e6 |
| | | | | 9 | 3 (T225) | 24-Nov-09 | 6.750E+04 | 3.98E+06 | 86.2% | 3.43E+06 | 5.88 | 58.07 | 171 | 29.1 | 1-Dec-09 | 3 x 1.2e6 |
| | | | | 10 | 3 (T225) | | 6.750E+04 | | | 0.00E+00 | | | | | | |

| Tube # | O₂ Level | Growth Medium | Seeding Density | Passage | # of Flasks | Seed Date | Seed Cell # | Cell Count (Harvest) | Viability (%) | TVC | Mean Dbl | Total Dbl | Passage Time (Hr) | Dbl Time ($T_D$) | Harvest Date |
|---|---|---|---|---|---|---|---|---|---|---|---|---|---|---|---|
| Epidural Connective Tissue | Low | FGM-2 | 100,000/cm² | 0 | 1 Well of a 6-well dish (3.8 cm²) | 29-Sep-09 | 1.900E+05 | 1.33E+05 | | | -0.51 | -0.51 | 161 | -315.1 | 5-Oct-09 |
| | | | 100/cm² | 1 | 3 (T225) | 5-Oct-09 | 6.750E+04 | 1.01E+07 | 94.4% | 9.49E+06 | 7.22 | 7.22 | 167.5 | 23.2 | 12-Oct-09 | 6 x 1.4e5 |

FIG. 4

Lazarus GM1 Study

GBT Sheep Fibroblasts in FGM-2, Low O2 - Summary

Total Doublings

| Passage | Lung | Epidural Connective Tissue |
|---|---|---|
| 0 | -0.78 | -0.51 |
| 1 | 7.30 | - |
| 2 | 13.73 | - |
| 3 | 20.02 | - |
| 4 | 27.00 | - |
| 5 | 33.54 | |
| 6 | 40.15 | |
| 7 | 46.46 | |
| 8 | 52.19 | |
| 9 | 58.07 | |

Yields

| Passage | Lung | Epidural Connective Tissue |
|---|---|---|
| 0 | 7.26E+06 | 1.33E+05 |
| 1 | 1.07E+07 | 1.01E+07 |
| 2 | 5.82E+06 | - |
| 3 | 5.27E+06 | - |
| 4 | 8.50E+06 | - |
| 5 | 6.30E+06 | |
| 6 | 6.60E+06 | |
| 7 | 5.33E+06 | |
| 8 | 3.60E+06 | |
| 9 | 3.98E+06 | |

FIG. 7

ND PURIFICATION OF GANGLIOSIDES

METHODS FOR EXTRACTION AND PURIFICATION OF GANGLIOSIDES

RELATED APPLICATIONS

This application is a continuation of International Application No. PCT/US10/47522, which designated the United States and was filed on Sep. 1, 2010, published in English, which claims the benefit of U.S. Provisional Application No. 61/238,775 filed Sep. 1, 2009, herein incorporated by reference in its entirety.

CROSS REFERENCE TO RELATED APPLICATIONS

This application is also related to PCT Application Nos. PCT/US10/47524; PCT/US10/47527; PCT/US10/47528 and PCT/US10/47520, all filed Sep. 1, 2010 and based on U.S. Provisional Application Nos. 61/238,726; 61/238,748, 61/238,735 and 61/238,712, each of which is incorporated by reference in its entirety.

FIELD

Described herein are methods for the extraction and purification of gangliosides, e.g., the monosialoganglioside (GM1).

BACKGROUND

Parkinson's disease (PD) is a slowly but relentlessly progressive, neurodegenerative disorder resulting in a time-dependent worsening of clinical symptoms. Clinical symptoms include tremor, bradykinesia (slowed motion), rigid muscles, impaired posture and balance, loss of automatic movements, and speech changes. Although there is considerable clinical variability between patients, the current armamentarium of anti-PD drugs effectively, if albeit temporarily, ameliorates most of the major Parkinsonian signs and symptoms in a majority of patients. Despite transient symptomatic improvements from traditional drug therapies, functional disability worsens over time.

The advent of levodopa therapy has been associated with a prolongation of survival in PD patients although this therapy does not slow the progression of symptoms. Levodopa, a metabolic pre-cursor of dopamine (L-3,4-dihydroxy phenylalanine), presently is the single most effective agent in the treatment of PD. Administered in connection with levodopa to prevent the catabolization of levodopa administered orally or catechol-O-methyltransferase (COMT) inhibitors such as tolcapme and entracapone; therefore, increasing the plasma half-life and the percentage of levodopa that reaches the CNS. A continuing problem with levodopa therapy is that after a long efficacy period in patients, the effectiveness in reducing symptoms last shorter after each dose. Additionally, dyskinesia occurs over time. These effects of continued use of levodopa are a result of progressive dopamine degeneration.

No drug has yet been identified that definitively slows or stops the progression of PD or substantially forestalls the inevitable functional decline in PD patients.

Drugs that can modify clinical progression, remediate motor or cognitive deficits, restore or enhance function of residual parts of the dopamine ("DA") system or activate compensatory mechanisms are sorely needed. No agent studied to date, however, has yielded convincing evidence of neuroprotection or disease modification and no agent has been studied as a neurorestorative agent.

Preclinical in vitro and in vivo studies have shown GM1 to rescue damaged DA neurons, stimulate survival and repair of dopaminergic neurons and sprouting of functional dopaminergic terminals, increase DA levels in the striatum and up-regulate DA synthetic capacity of residual neurons. See, e.g., "GM1 Ganglioside in the Treatment of Parkinson's Disease," Schneider, Ann. N.Y. Acad. Sciences 845, 363-73 (February 2006). Preliminary clinical studies of GM1 in PD patients also showed clinical improvements in patients with short-term use of GM1 and minimal symptom progression in a sub-group of patients followed over five years of GM1 use followed by significant progression of symptoms following discontinuation of long-term GM1 use.

Therefore, a potentially fruitful approach to the treatment of PD consists of administration of agents such as GM1, which may stabilize injured or dying DA neurons, stimulate sprouting of new dopaminergic fibers and terminals, or enhance the function of residual dopaminergic neurons or stimulate or maintain compensatory processes.

GM1, a monosialoganglioside, is a normal constituent of nerve cell membranes, and is known to modulate a number of cell surface and receptor activities as well as play important roles in neuronal differentiation and development, protein phosphorylation, and synaptic function. In numerous pre-clinical studies, chronic treatment with GM1 following different types of lesions to the central nervous system has resulted in biochemical and behavioral recovery and these effects have been particularly impressive in the damaged DA system.

Heretofore, the only form of GM1 clinically used has been derived from bovine brain. The limited amount of GM1 obtained per brain and the cost associated with brain extraction procedures have limited its development as a commercial product. Moreover, using cow's brain as a GM1 source raises justifiable concerns over prion diseases such as bovine spongiform encephalopathy ("mad cow disease").

A continuing and unmet need exists for new and improved methods for the extraction and purification of GM1, particularly methods using non-bovine sources.

SUMMARY

This invention discloses new methods for the extraction and purification of gangliosides, e.g., the monosialoganglioside GM1, from non-bovine sources.

Provided for herein is a method of isolating GM1 ganglioside by preparing non-bovine and non-porcine tissues comprising GM1 producer cells which includes isolating from tissues the GM1 ganglioside producing cell; expanding GM1 producer cell in culture under suitable conditions to facilitate expansion of said cells; expressing GM1 ganglioside expression in culture under suitable conditions; isolating GM1 ganglioside from culture. The GM1 producing cells can be neural cells. In another aspect, the cells can be fibroblast cells. As used herein, GM1 producer cells are cells which express GM1 either basally or at an elevated level as compared to normal cells.

In another embodiment the method may comprise isolating GM1 from neural cell which is derived from non-bovine and non-porcine fibroblast cells harvested from subjects with GM1-gangliosidosis type-I. Therefore the GM1 is free of BSE contaminants.

In another embodiment a GM1 ganglioside composition provided wherein the GM1 ganglioside composition is produced by process disclosed herein comprising preparing non-bovine and non-porcine tissues comprising GM1 producer cells; isolating from said tissues the GM1 ganglioside producing cell; expanding said GM1 producer cell in culture under suitable conditions to facilitate expansion of said cells; expressing GM1 ganglioside expression in culture under suitable conditions; isolating said GM1 ganglioside from said culture. Therefore, the GM1 ganglioside is substantially free of or free of BSE contaminants.

Additional features may be understood by referring to the following detailed description and examples.

BRIEF DESCRIPTION OF FIGURES

FIG. 1 depicts a table listing expansion statistics of sheep hippocampal cells in low $O_2$ culture in media type 1 as described herein.

FIG. 3 depicts a table listing total doublings and yields of hippocampal cells in low $O_2$ culture in media type 1 as described herein.

FIG. 4 depicts a table listing expansion statistics of sheep fibroblast cells in low $O_2$ culture in media type 1 as described herein.

FIG. 7 depicts a table listing fibroblast lung versus connective tissue expansion.

DETAILED DESCRIPTION

Figure 2:
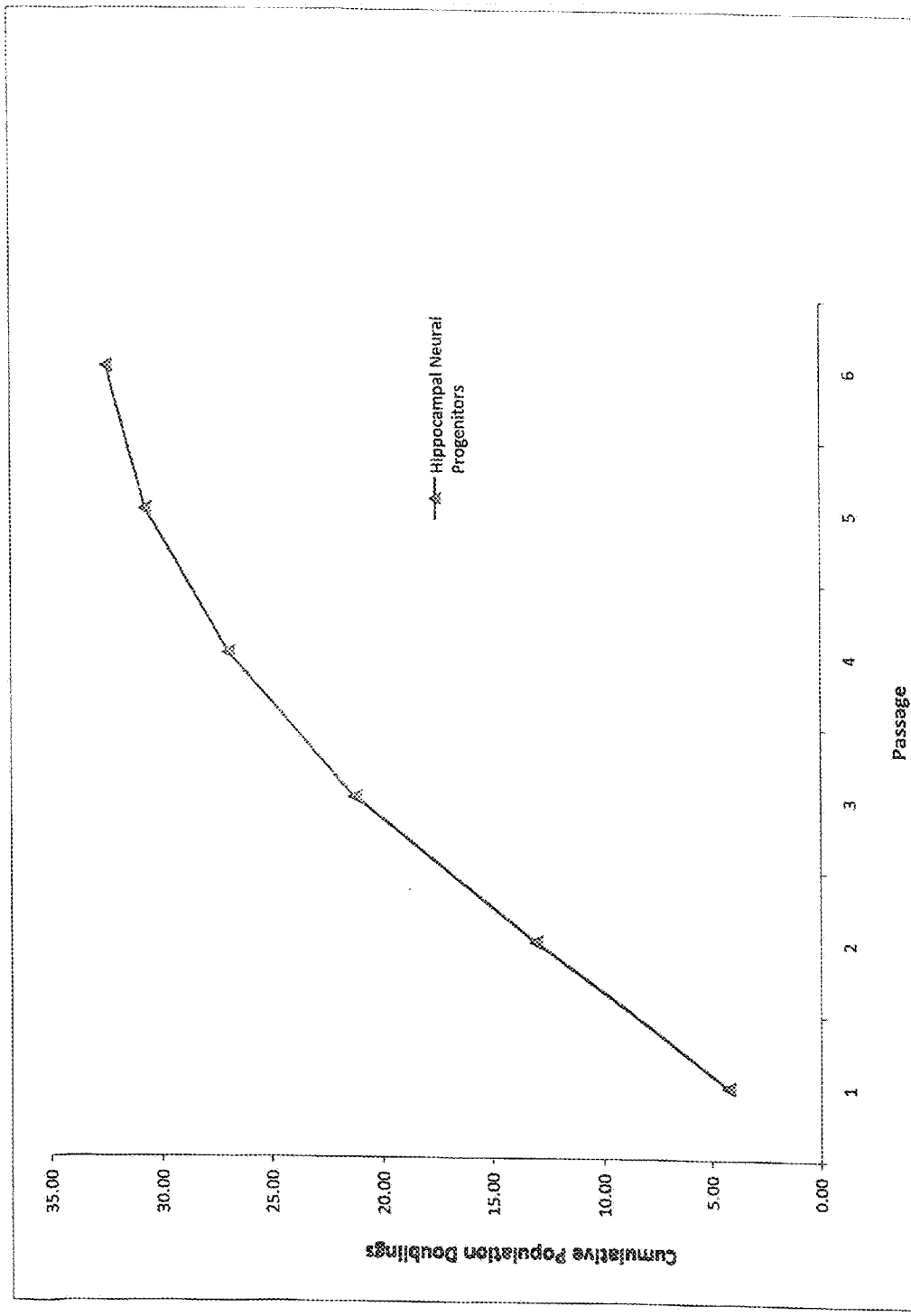
FIG. 2 depicts a line graph of cumulative population doublings of hippocampal neural progenitor cells.
Figure 5:
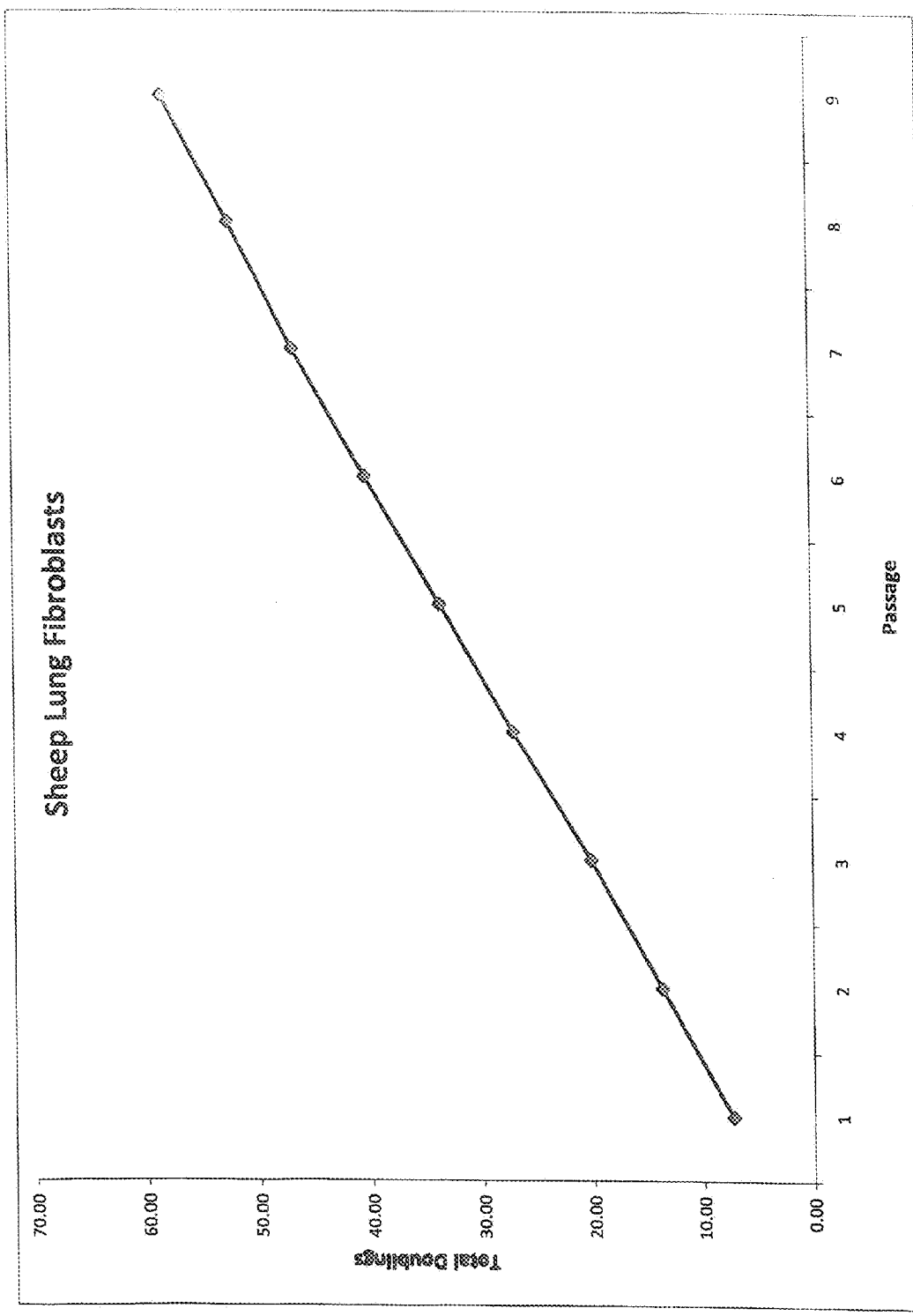
FIG. 5 depicts a line graph of cumulative populations doublings of sheep fibroblast cells.
Figure 6:
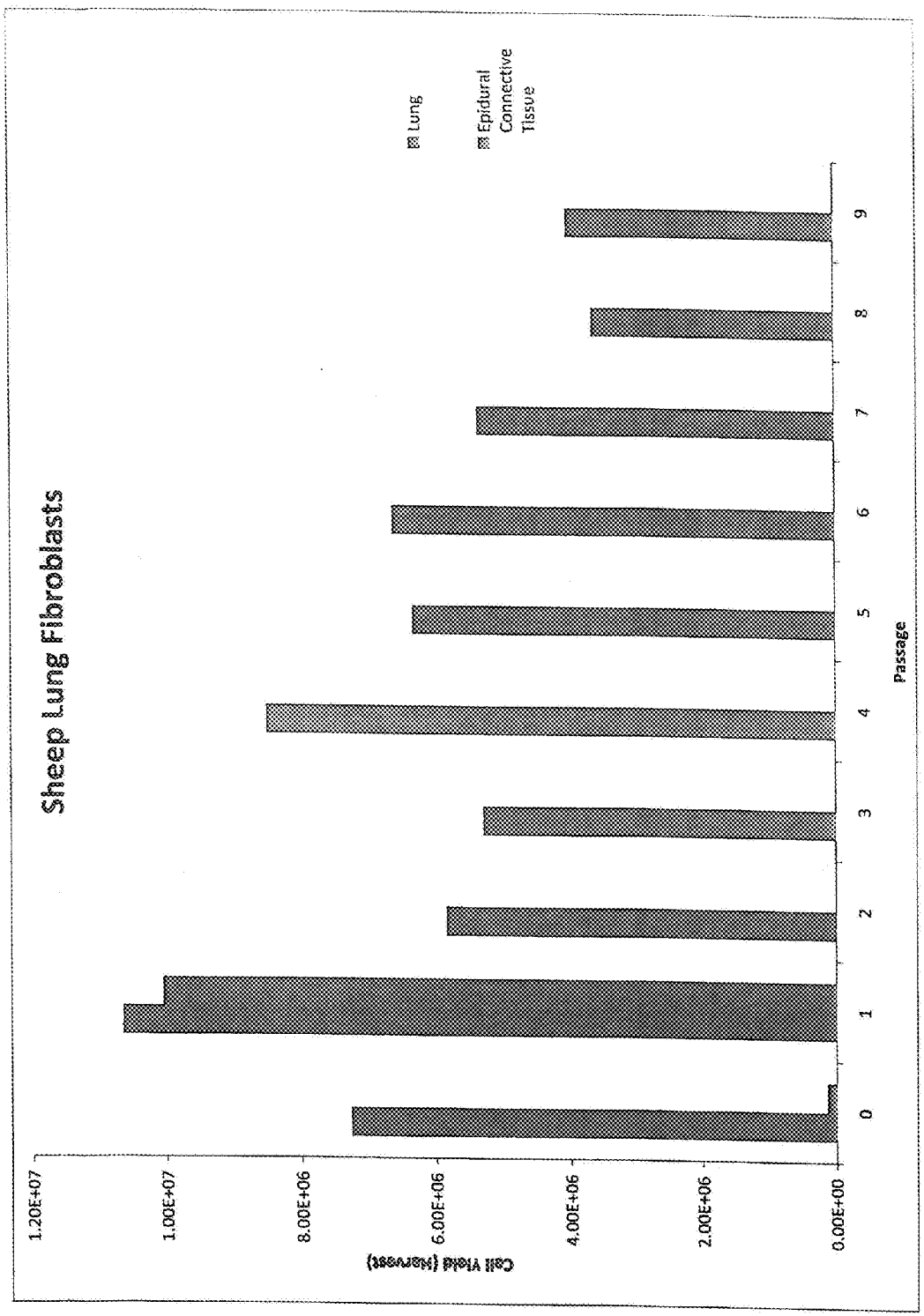
FIG. 6 depicts a bar graph depicting lung versus epidural connective tissue expansion.

Described herein are new methods for purification and extraction of GM1 ganglioside from cells derived from sheep afflicted with GM1 gangliosidosis or from cells derived from human patients with GM1 gangliosidosis as stable and renewable sources of GM1.

Provided for herein is a method of isolating GM1 ganglioside by preparing non-bovine and non-porcine tissues comprising GM1 producer cells which includes isolating from tissues the GM1 ganglioside producing cell; expanding GM1 producer cell in culture under suitable conditions to facilitate expansion of said cells; expressing GM1 ganglioside expression in culture under suitable conditions; isolating GM1 ganglioside from culture. The GM1 producing cells can be neural cells. In another aspect, the cells can be fibroblast cells. As used herein, GM1 producer cells are over-producing cells which express GM1 at an elevated level as compared to normal cells. In particular, such cells can be derived from gangliosidosis afflicted sheep and/or humans.

The tissues from which the cells are isolated and prepared include the centrum semiovale, cerebellar cortex, hippocampus, head of caudate, frontal lobe, parietal cortex, or ventricular wall, subgranular zone or ventricular lining regions of the brain. Any combination of cells extracted from these different regions may be expanded and cultured in the present method. The GM producer cells are fibroblast cells derived from epidermal tissues or lung tissue, where the GM1 producer cells include core brain tissue cells or progenitor cells.

Also another aspect disclosed is a method of preparing non-bovine or non-porcine tissues by excising portions of tissues; fixing said tissues in a transport media, where the media can be high glucose DMEM; 4 mM L-glutamine, 5-10%, 10-20%, or 20-30% fetal bovine serum, MEM non-essential amino acids solution 1×, penicillin 100 U/ml, streptomycin; amphomycin, and gentamycin; and refrigerating tissues at a temperature sufficient to maintain expansion of said cells.

In an embodiment, the neural cell is derived from a brain tissue where GMa gangoside overexpressed, or derived from a brain affected with GM1 gangliosidosis. The neural cells may have a deficiency in β-galactosidase that lead to overexpression in GM1 as compared to normal. The neural cells used in the method may have partial a-neuraminidase activity.

In another embodiment the method may comprise isolating GM1 from non-bovine and non-porcine fibroblast cells harvested from human subjects with GM1-gangliosidosis type-I. Therefore the GM1 is free of BSE contaminants. BSE contaminants as used herein means any biomolecule proteins, prion protein (PrP) or any biomolecule that may be detected via antibodies to PrP proteins. Typically, commercially available sources of GM1 are from bovines and can be found in irradiated form to remove possible contaminants, however the therapeutic risk of such a source remains. Such typical GM1 sources include Sigma Aldrich.

In another embodiment a GM1 ganglioside composition provided wherein the GM1 ganglioside composition is produced by process disclosed herein comprising preparing non-bovine and non-porcine tissues comprising GM1 producer cells; isolating from said tissues the GM1 ganglioside producing cell; expanding said GM1 producer cell in culture under suitable conditions to facilitate expansion of said cells; expressing GM1 ganglioside expression in culture under suitable conditions; isolating said GM1 ganglioside from said culture. Therefore, the GM1 ganglioside is substantially free of or free of BSE contaminants.

This invention involves the use of cells derived from sheep afflicted with GM1 gangliosidosis or cells derived from humans with GM1 gangliosidosis to obtain commercially viable quantities of GM1 ganglioside for use in treatment of Parkinson's disease and other neurological disorders. Gangliosides may be administered alone or together with standard medical care for PD patients, or patients with other types of neurodegenerative diseases including, but not limited to, Huntington's Disease, etc.).

GM1 alone or in combination with other gangliosides may be administered via subcutaneous or intravenous injection or nasal or mucosal administration, among others. This may also include prolonged action dosage forms, and gangliosides may be administered using controlled release formulations (liposomes, nanoparticles, microspheres) to prolong drug activity. They may also be conjugated to appropriate transporter molecules in order to cross the blood brain barrier.

Sheep afflicted with GM1 gangliosidosis and the extraction of GM1 and other gangliosides from the brains of such animals are described in U.S. Pat. No. 5,532,141, which is incorporated herein by reference in its entirety. The disease in these animals is characterized by a deficiency in β-galactosidase activity and partial a-neuraminidase activity, resulting in animals with accumulation of large amounts of GM1 ganglioside in brain tissue (up to 40 fold increase compared to non-affected animals). With optimized extraction procedures, it is estimated that a single gangliosidosis sheep brain would yield 1-2 grams of GM1. It is further estimated that 1 kg of affected brain would yield approximately 15 g of GM1. In comparison, 1 kg of porcine brain is estimated to yield 250 mg of GM1. However, even at these enhanced levels of expression, several hundred thousand sheep per year would be necessary to obtain commercial quantities of GM1.

Using cell technologies, GM1 may be obtained from several potential sources derived from GM1 gangliosidosis sheep. For example, one may grow and expand neural precursor cells, drive them toward a neuronal phenotype, optimize their growth and development (and perhaps even GM1 production using various manipulations, including but not limited to inhibiting B-series ganglioside production (e.g., by inhibiting GD3 synthase) and halting the biosynthetic pathway for A-series gangliosides at GM1, thus shunting more ganglioside production toward GM1) and then extract GM1 from cultured neural cells as well as GM1 shed by cells into the media. Further alterations can also be made to enhance ganglioside shedding and further optimize collection of ganglioside from cultured cells. Alternatively or in combination with the general scheme outlined above, fibroblasts or hepatocytes may also be grown in culture and used as sources of GM1.

Cells used in the present method maybe derived from brain tissues including, but not limited to, centrum semivale, cerebellar cortex, hippocampus, caudate nucleus, cerebral cortex, ventricular wall or a combination thereof.

Another potential source of GM1 are fibroblasts (or hepatocytes) from patients with type-I (infantile) GM1 gangliosidosis. Patients with GM1-gangliosidosis type-I tend to have less than 1% of the normal amount of β-galactosidase in their cells and thus their cells tend to produce very high levels of GM1 ganglioside. Normal human fibroblasts can contain approximately 0.7 nmoles GM1/mg protein. GM1 gangliosidosis fibroblasts can contain up to 2.58 nmoles GM1/mg protein. The amount of GM1 obtained from cultured human GM1 gangliosidosis fibroblasts will be optimized using optimal cell growth parameters, culture and feeding conditions, and by determining optimal time to harvest cells for GM1 extraction. Additionally, numerous samples will be screened from GM1 type-I patient donors to find cell lines that present optimal GM1 accumulation due to the severity of β-galactosidase deficit, which will differ from patient to patient. Additionally, hepatocytes from the same patients may be used as an alternative or complementary cell source of GM1.

Once we have cells form gangliosidosis sheep there are several possible ways to even further enhance the GM1 yield from these cells. One method would be to treat the cells with low concentrations of chloroquine, a weak base, which will cause a marked accumulation of GM1 in endosomes and on the surface of cells (Yuyama et al., 2006). Another method would be to treat the cells with sialidase (neuraminidase) which will convert all of the major brain complex gangliosides (ex., GD1a, GD1b, and GT1b) to GM1 on intact cells (Schauer, et al, 1980). Another method would be to use a nonenzymatic method using Dowex-50W-H+ to catalyze the highly selective desialylation of polysialated ganglio-N-tetraose series gangliosides to yield primarily GM1 (Schengrund and Kovac, 1999). Using these methods it is possible to retrieve enhanced amounts of GM1 from cells and membranes as well as increase the amount of GM1 shed into and retrieved from the media.

An additional potential means for producing GM1 ganglioside by cell-based technology may include programming cells by multiplex genome engineering and accelerated evolution to induce *E. coli* to produce GM1 ganglioside. Using multiplex automated genome engineering ("MAGE"), one may engineer the biosynthetic pathway for GM1 in *E. coli* in order to overproduce GM1 ganglioside. For example, one may simultaneously modify many genomic locations to modify GM1 biosynthesis with certain relevant genes having optimally tuned expression and certain genes being inhibited or omitted in order to optimize GM1 production and inhibit production of other gangliosides. *E. coli* may be modified by methods known to those of skill in the art whereby ganglioside genes are incorporated into the *E. coli* system via standard methods are as are known in the art. By way of example, standard methods include isolating plasmid DNA which have been modified to express GM1 synthase to produce GM1 in culture. Other ganglioside producing genes include GD3 synthase.

*E. coli* may be grown under specific conditions in which precursor substances are available in the media, as necessary, such as synthetic lactosylceramide (LacCer, plant source) and sialic acid (available from non-animal source or can be synthesized). Enzymatic activity (e.g., sialyltransferase, N-acetyl galactosaminyltransferase, galactosyltransferase) may be fine tuned by the MAGE process, and activator (guanosine triphosphate for activation of the transferase enzyme) may be provided, as well as N-acetyl galactosamine and galactose (the sugars need to be converted to their nucleotide derivatives in order to serve as sugar donors).

GM1 is currently extracted from bovine or porcine brain, which is a low-yield, expensive process. The current invention would provide for a safe and efficient cell-based production of GM1 ganglioside. It would also provide for the first commercial source of human GM1 ganglioside. Other ganglioside species besides GM1 may also be produced with this technology, and the GM1 and other gangliosides may have uses in a wide variety of neurological disorders such as Parkinson's disease.

A typical procedure for the extraction, separation and purification of brain gangliosides is described, which involves: exhaustive extraction of brain with buffered tetrahydrofuran or other appropriate solvents as are known in the art; partition of the extract first with ethyl ether, then with distilled water; dialysis of the obtained aqueous phase, and chromatography of the dialyzed solution of silica gel column. The residue after exhaustive extraction contains all brain glycoproteins. After procedures include chloroform method of the extraction process.

EXAMPLES

Example 1

Ovine brain tissues received, which include the following tissue sources: centrum semiovale; cerebellar cortex; hippocampus, caudate nucleus, cerebral cortex (ex., frontal, parietal), and ventricular walls.

All tissues were processed individually via the following method: Rinsed each tissue type with PIPES buffer solution; Digested each tissue in a cocktail of Papain/DNase I/Dispase (Neutral Protease) with antibiotics/antimycotics, neutralized the enzymes and passed dissociated cells through a cell strainer; Cells were centrifuged and resuspended in DMEM/F12/N2 containing 5% FBS containing antibiotics/antimycotics; Cells were enumerated then seeded in fibronectin-coated flasks in: a. Media Type #1: DMEM/F12/N2 containing 5% FBS containing antibiotics/antimycotics; supplemented with 10 ng/ml bFGF and 20 ng/ml EGF. Neurocult Proliferation-A medium; Cells in each media type were grown in a 37° C. humidified incubator under Low $O_2$ and High $O_2$ for comparison.

TABLE 1

Sheep Brain Tissue-Derived Cell Expansion Summary Table

| | Total Doublings/<br>Last Passage # |
|---|---|
| Low $O_2$ Cultures - Media Type #1 | |
| Centrum Semiovale | 16.1/P.2 |
| Cerebellar Cortex | 13.8/P.2 |

TABLE 1-continued

Sheep Brain Tissue-Derived Cell Expansion Summary Table

| | Total Doublings/ Last Passage # |
|---|---|
| Hippocampus | 21.1/P.3 |
| Head of Caudate | 8.9/P.1 |
| Frontal-Parietal Cortex | 2.1/P.1 |
| Ventricular Wall | 6.8/P.1 |
| High $O_2$ Cultures - Media Type #1 | |
| Centrum Semiovale | P.0 |
| Cerebellar Cortex | P.0 |
| Hippocampus | P.0 |
| Head of Caudate | P.0 |
| Frontal-Parietal Cortex | P.0 |
| Ventricular Wall | P.0 |

Table 1 above described the proliferation and expansion of cells in various growth conditions. It is noted that cultures grown in Neurocult Proliferation-A did not grow well so the small number of cells harvested at P.0 were frozen down and not expanded further.

Example 2

Ovine tissues received for fibroblast isolation, which include the following tissue sources: lung (left and right lungs were pooled), and epidural connective tissue.

All tissues were processed individually, using the following methods: Rinsed each tissue type with PIPES buffer solution. Digested each tissue in Collagenase/Hyalluranidase in DMEM with antibiotics/antimycotics, neutralized the enzymes in DMEM containing 10% FBS and passed dissociated cells through a cell strainer. Cells were centrifuged and resuspended in FGM-2 containing antibiotics/antimycotics. Cells were enumerated then seeded in flasks and remaining tissues in dishes in FGM-2 medium. Cells were grown in a 37° C. humidified incubator under Low $O_2$ tension only.

Sheep Fibroblast Expansion Summary Table

| | Total Doublings/ Last Passage # |
|---|---|
| Lung | 20/P.2 |
| Epidural Connective Tissue | 7.2/P.1 |

Example 3

Digestion

Specimens were received in various centrifuge tubes, labeled 1-10, and were removed from the shipping box, wiped down and placed into a 50 mL tube rack. Images of each tube were captured. Each tube was sprayed with ethanol, wiped down again, and then transferred to the Biosafety Cabinet for aseptic processing. The transport medium from each tube was carefully aspirated out using a clean 10 mL pipette and ejected into a waste container. Excess (40 mL) PIPES solution was transferred into each tube, the cap was replaced and tubes were gently inverted back and forth several times to rinse away residual transport medium from the tissues. This was then aspirated out using a 10 mL pipette and ejected into a waste container.

Twenty milliliters brain digestion medium was transferred into tubes containing brain tissue and each tube was labeled 1 through 6. A key was made to later translate the area of the brain associated with each number. Twenty milliliters collagenase/hyaluronidase (1×) solution was transferred to each of the tubes containing tissues from other organs. Using a sterile 25 ml and 50 ml pipette, sterile forceps and scalpel, tissues from each of tube was transferred to a sterile 10 cm dish, bathed in digestion medium and minced into very small sections. The contents of each dish (tissue pieces and digestion medium) was pipetted up with a 25 mL or 50 mL pipette and transferred back into the appropriate tube, capped and all were placed into the 37° C. incubator for 45 minutes. After 45 minutes, the tubes were aseptically transferred back into the hood and each was triturated using a sterile 25 mL and 10 mL pipette, respectively. The caps were replaced and the tubes were placed back in the tube rack in the 37° C. incubator for 15 minutes. After incubation, tubes were aseptically transferred into the hood. Twenty-five milliliters Neutralization medium was transferred into each of the 10 tubes, tubes were capped and each inverted back and forth several times to mix. Tubes were centrifuged for 10 minutes at 200 g to pellet cells and remaining tissue chunks. Tubes were aseptically transferred into the hood and the supernatant was carefully aspirated from each tube, being sure not to suck up any tissue pieces or cells. Tubes containing brain regions 1-6 received 40 mL Media Type #1 to re-suspend the cells and remaining tissue pieces. Tubes containing lung, epidural connective tissue and bone connective tissue were resuspended in 40 mL FGM-2 fibroblast growth medium. Each of the 10 tubes with resuspended cells and tissues were pipetted through a 40 um cell strainer and into the new, labeled 50 mL tubes. A count and viability was performed on each tube.

Low $O_2$ Expansion Conditions.

Cells from six different regions of the brain were seeded at 100,000/cm$^2$ in six fibronectin coated T80 flasks in 15 ml of Media Type #1 or 15 mL Media Type #2 (Neurocult Proliferation-A medium) and incubated in a humidified 37° C. incubator at low oxygen tension (4% $O_2$, 5% $CO_2$ and balanced with Nitrogen). Every two days 50% of the culture medium was replaced with fresh medium. Cultures were non-homogenous. Colony forming cells were the minority of the cells present early on, but after a few days these cells began forming colonies and growing. Passage 0 cultures were harvest on Day 9. See Table 1 for yields.

Passage 1 cells were seeded at 100 cells/cm$^2$ in two T225 cm$^2$ fibronectin coated flasks in 36 ml of both Media Type #1 and Media Type #2 for each of the six regions. Cultures were fed with 100% fresh medium on Day 5. Cultures were still non-homogenous during this passage but have cleaned up significantly and there are many more colony forming cells present early in this passage and these cells grew faster than the previous passage. Images were captured at 4×, 100×, 200× on Day 6. Cultures were harvested on Day 6.

Passage 2 cells were seeded at 100 cells/cm$^2$ in two T225 cm$^2$ fibronectin coated flasks in 36 ml of both Media Type #1 and Media Type #2 for each of the six regions. Cultures were fed with 100% fresh medium on Day 5. Cultures were ≥90% homogenous. Cultures were harvested on Day 6. All cultures maintained in Media Type #2 were then frozen down and not expanded further. Culture maintained in Media Type #1 (i.e. Hippocampal Neural Progenitors) were further sub-cultured to passage six (below):

Passage 3 cells were seeded at 100 cells/cm$^2$ in two T225 cm$^2$ fibronectin coated flasks in 36 ml of Media Type #1. Cultures were fed with 100% fresh medium on Day 5. Cultures appeared to be homogeneous this passage. Images were captured at 4×, 100×, 200× on Day 6. Cultures were harvested on Day 6.

Passage 4 cells were seeded at 100 cells/cm² in two T225 cm² fibronectin coated flasks in 36 ml Media Type #1. Cultures were fed with 100% fresh medium on Day 5. Images were captured at 4×, 100×, 200× on Day 6. Cultures were harvested on Day 6.

Fibroblasts. Cells from the digestion of Sheep lungs were seeded at 100,000/cm² and epidural connective tissue were seeded at 50,000/cm² in FGM-2 medium. Cultures were fed with 50% fresh medium every 2 days and Passage 0 harvested on Day 5. Both cultures were passaged at lower density and remainder were frozen and banked.

Passage 1 epidural and lung fibroblasts were seeded at 100/cm² in FGM-2 medium in T225 cm² flasks. Cultures were fed with 100% fresh FGM-2 medium on Day 5 and harvested on Day 7. Lung cultures were passaged and remainder was frozen and banked. Epidural fibroblasts were all frozen and banked.

Passage 2 lung fibroblasts were seeded at 100/cm² in FGM-2 medium in T225 cm² flasks. Cultures were fed with 100% fresh FGM-2 medium on Day 4 due to being heavy then harvested on Day 5. Cultures were passaged and remainder was frozen and banked.

Passage 3 lung fibroblasts were seeded at 100/cm² in FGM-2 medium in T225 cm² flasks. Cultures were fed with 100% fresh FGM-2 medium on Day 5 and harvested on Day 6. Cultures were passaged and remainder was frozen and banked.

High $O_2$ Conditions (Standard Method). Cells from each of the six regions were seeded in four T25 cm² and one T80 cm² (all coated with fibronectin) at 100,000/cm² in 5 ml and 13 ml, respectively, of Media Type #1 and Media Type #2 and incubated in a humidified 37° C. incubator at 18% $O_2$, 5% $CO_2$ (Standard conditions). Cultures were fed with their respective media on Day 5 then harvested 24 hours later on Day 6. Images were captured at 4×, 100×, 200× on Day 6 prior to harvest. Cells from all regions were counted then frozen and banked.

Transport Medium. Media used for storage of tissues post mortem and during transit. Components: High glucose DMEM (Invitrogen); 4 mM L-Glutamine (Hyclone); 20% Fetal Bovine Serum (Hyclone); MEM Non-Essential Amino Acids Solution, 1× (Invitrogen, Catalog #11140, 100×Soln., Lot #672555); Penicillin (100 U/ml), Streptomycin (ug/ml), Ampho (/ml) (Stem Cell Technologies, Inc., Catalog #, 100× Solution, Lot #); Gentamycin (50 ug/ml).

Digestion Medium.

Brain: High glucose 1:1 DMEM:F12: 4 mM L-Glutamine; Dispase (1 U/ml) (Roche, Catalog #04942086001); DNase (250 U/ml) (Invitrogen, Catalog #18047-019); Papain (2.5 U/ml) (Sigma, Catalog #76218); Penicillin (100 U/ml), Streptomycin (ug/ml), Ampho (/ml) (Stem Cell Technologies, Inc., Catalog #, 100× Solution); Gentamycin (50 ug/ml) (Sigma);

Lung, Epidural and Bone: High glucose DMEM: 4 mM L-Glutamine; Collagenase (300 U/ml)/Hyaluronidase (100 U/ml) (Stem Cell Technologies); Hyaluronidase (Stem Cell Technologies); Penicillin (100 U/ml), Streptomycin (ug/ml), Ampho (/ml) (Stem Cell Technologies, Inc.); Gentamycin (50 ug/ml).

4. Culture Medium Brain:

a. Media Type #1. High glucose 1:1 DMEM:F12; 4 mM L-Glutamine; N2 Supplement (100×) liquid (Invitrogen); Penicillin (100 U/ml), Streptomycin (ug/ml), Ampho (/ml) (Stem Cell Technologies, Inc.,); Gentamycin (50 ug/ml); 20 ng/ml Epidermal Growth Factor, Human, recombinant (rh EGF) (Stem Cell Technologies); 10 ng/ml basic Fibroblast Growth Factor, Human, recombinant (rh bFGF) (Stem Cell Technologies).

b. Media Type #2: Neurocult NS-A Proliferation Media. Neurocult NS-A Basal Medium (Human), 450 ml (Stem Cell Technologies); Neurocult NS-A Proliferation Supplements (Human), 50 ml (Stem Cell Technologies); Penicillin (100 U/ml), Streptomycin (ug/ml), Ampho (/ml) (Stem Cell Technologies, Inc.,); Gentamycin (50 ug/ml); 20 ng/ml Epidermal Growth Factor, Human, recombinant (rh EGF) (Stem Cell Technologies,); 10 ng/ml basic Fibroblast Growth Factor, Human, recombinant (rh bFGF) (Stem Cell Technologies)

Example 4

In a clinical trial treating Parkinson's disease patients with GM1, all functional assessments (during baseline and all subsequent visits) took place in the morning prior to the patient taking the first dose of anti-Parkinson medication and at least 12 hrs. since the previous dose of medication (considered to be a practically defined "off" period). All patients were tested on three separate occasions (within a two-week period) for baseline performance on the following functional measures: (1) Unified Parkinson's Disease Rating Scale ("UPDRS"), rated independently by a principal and secondary raters; (2) time to perform: 20 pronations/supinations of the hands; 20 heel-toe taps; 20 thumb-index finger taps; time to touch thumb sequentially to other fingers 10 times; time to walk 20 feet as quickly as possible, turn around, and return to the starting point; simple reaction time assessment; (3) test of sensorimotor integration in which the patient needed to produce specific movements based only on somatosensory and proprioceptive feedback. The testing was performed at four monthly follow-up visits.

A mean baseline score for each patient was calculated and used for comparison with treatment scores. The principal efficacy measure was change in the motor component of the UPDRS, a standard clinical assessment tool. The GM1-treated group (N=22) showed significant improvements on UPDRS motor scores (mean improvement of 5.05 points at week four and 7.53 points at week 16) whereas mean scores for the placebo-treated group were essentially unchanged over the 16 weeks of treatment. The treatment effect sizes at week four (−5.95±1.12), week eight (−5.61±1.39), week 12 (−5.37±1.30) and week 16 (−6.79±1.24) were statistically significant (ANCOVA, p<0.0002). Secondary assessments of motor function showed that while both groups made a similar number of errors on the sensorimotor integration task at baseline (GM1=5.3±2.3; placebo=5.4±3.1), GM1-treated patients made significantly fewer errors after 16 weeks of treatment (0.7 errors±0.8) than did placebo-treated patients (5.1 errors±3.1, p=0.0001). The GM1-treated group also performed the timed motor tasks (i.e., pronation/supination (p=0.0001), heel/toe tapping (p=0.0008), finger tapping (p=0.0001), sequential finger tapping (p=0.0001), and walking (p=0.02) significantly faster at week 16, compared to baseline, than were placebo-treated patients. At the end of 5 years of open use of GM1, patients had lower UPDRS motor scores and were reporting fewer problems with their "off" period activities of daily living than at pre-randomization baseline.

Once baseline testing was completed, patients received an intravenous infusion of either 1,000 mg GM1 ganglioside or placebo (i.e., diluent without GM1) in 50 mL sterile Ringer's solution. Patients were taught to self-administer a subcutaneous injection and were sent home with a four week supply of either GM1 ganglioside (100 mg GM1 in 2.0 ml of vehicle/ vial) or placebo, provided in identical 2.0 mL vials. Patients were instructed to administer the contents of two vials per day, one in the morning and one in the evening (total daily dose=200 mg GM1. Concomitant medications were kept constant.

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

[1] Neeta S. Roy, et al. 2000. J Neurosci 59:321-31.
[2] (Philip H. Schwartz, et al. 2003. J Neurosci; 74:838-51.

The invention claimed is:

1. A culture-based method of isolating GM1 ganglioside comprising:
   (a) expanding a GM1 ganglioside producing cell obtained from tissue that is non-bovine and non-porcine in culture, wherein said cell is a neural cell or fibroblast cell, and wherein said culture comprises 4% oxygen; and
   (b) expressing GM1 ganglioside in the GM1 producing cells in (a); and
   (c) isolating the GM1 ganglioside expressed in (b).

2. The method of claim 1, wherein the GM1 producing cell is a neural cell.

3. The method of claim 2, wherein said neural cell is obtained from a brain tissue wherein GM1 ganglioside is overexpressed.

4. The method of claim 2, wherein said neural cell is obtained from a brain affected with GM1 gangliosidosis.

5. The method of claim 2, wherein said neural cell comprises a deficiency in β-galactosidase.

6. The method of claim 2, wherein said neural cell comprises partial α-neuraminidase activity.

7. The method of claim 2, wherein said neural cell is obtained from human fibroblast cells harvested from subjects with GM1-gangliosidosis type-I.

8. The method of claim 1 wherein said GM1 producing cell is a fibroblast cell.

9. The method of claim 1, wherein said tissue is selected from the group consisting of centrum semiovale, cerebellar cortex, hippocampus, head of caudate, frontal lobe, parietal cortex, ventricular wall, subgranular zone, ventricular lining region of a brain, and any combination thereof.

10. The method of claim 9, further comprising preparing said tissue before said isolating, wherein said preparing comprises excising portions of tissues; fixing said tissues in a transport media, wherein said media comprises high glucose DMEM; 4 mM L-glutamine, 5-10%, 10-20%, or 20-30% fetal bovine serum, MEM non-essential amino acids solution 1×, penicillin 100 U/ml, streptomycin; amphomycin, and gentamycin; and maintaining said tissues at a temperature sufficient to maintain expansion of said cells.

11. The method of claim 1, wherein said GM1 producing cell is a fibroblast cell obtained from epidermal tissues or lung tissue.

12. The method of claim 1, wherein said GM1 producing cell is a core brain tissue cell.

13. The method of claim 1, wherein said GM1 producing cell is a progenitor cell.

14. The method of claim 1, wherein the GM1 producing cell of step (a) overexpresses GM1.

15. The method of claim 1, wherein the GM1 producing cell is obtained from tissue affected with GM1 gangliosidosis.

16. The method of claim 1, wherein the expressing step (b) comprises contacting the GM1 producer cells with chloroquine in an amount effective to enhance expression of GM1 ganglioside in the cell culture as compared to the amount of GM1 expressed in the GM1 producer cells in the absence of chloroquine.

17. The method of claim 1 wherein the producing cell is obtained from sheep or human tissues.

* * * * *